(12) United States Patent
Sharma et al.

(10) Patent No.: US 8,565,898 B2
(45) Date of Patent: Oct. 22, 2013

(54) RATE CONTROL DURING AF USING CELLULAR INTERVENTION TO MODULATE AV NODE

(75) Inventors: Vinod Sharma, Blaine, MN (US); Daniel C. Sigg, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 1058 days.

(21) Appl. No.: 11/116,621

(22) Filed: Apr. 28, 2005

(65) Prior Publication Data

US 2006/0247697 A1    Nov. 2, 2006

(51) Int. Cl.
*A61N 1/00*     (2006.01)
*A61K 38/00*    (2006.01)
*A61K 38/16*    (2006.01)

(52) U.S. Cl.
USPC .......................... 607/122; 514/12.1; 514/17.4

(58) Field of Classification Search
USPC ................................ 607/122; 514/12.1, 17.4
See application file for complete search history.

(56) References Cited

U.S. PATENT DOCUMENTS

| | | | |
|---|---|---|---|
| 4,882,777 A * | 11/1989 | Narula | 604/532 |
| 5,836,985 A * | 11/1998 | Rostami et al. | 607/14 |
| 6,718,206 B2 * | 4/2004 | Casavant | 607/9 |
| 6,852,704 B1 | 2/2005 | Levy et al. | |
| 7,294,333 B1 * | 11/2007 | Feld et al. | 424/93.21 |
| 2002/0155101 A1 | 10/2002 | Donahue et al. | |
| 2004/0005295 A1 | 1/2004 | Lee et al. | |
| 2005/0008628 A1 | 1/2005 | Feld et al. | |
| 2005/0065565 A1 * | 3/2005 | Kramer et al. | 607/9 |

FOREIGN PATENT DOCUMENTS

| WO | WO2004093969 A1 | 11/2004 |
|---|---|---|
| WO | WO2005009477 A1 | 2/2005 |

OTHER PUBLICATIONS

Viswanathan et al. Recreating an artificial biological pacemaker: insights from a theoretical model. Heart Rhythm. 3(7): 824-31, 2006.*
Miake et al., Biological pacemaker created by gene transfer, Nature, 419(6903): 132-3, 2002.*
Plotnikov et al., Biological pacemaker implanted in canine left bundle branch provides ventricular escape rhythms that have physiologically acceptable rates. Circulation, 109(4): 506-12, 2004.*
Kabb et al., Molecular basis of transient outward potassium current downregulation in human heart failure: a decrease in Kv4.3 mRNA correlates with a reduction in current density. Circulation, 98 (14): 1383-93, 1998.*
Gillis et al., Heart block in mice overexpressing calcineurin but not NF-AT3. Cardiovasc Res. 64(3):488-95, 2004.*
Grunnet et al., The voltage-gated potassium channel subunit, Kv1.3, is expressed in epithelia. Biochim Biophys Acta. 1616(1):85-94, 2003.*
Hoshijima Masahiko et al. "Chronic suppression of heart-failure progression by a pseudophosphorylated mutant of phospholamban via in vivo cardiac rAAV gene delivery", Nature Medicine, Aug. 2002, pp. 864-871, vol. 8, No. 8, Nature Publishing Group, New York, NY, US.
Michael R. Rosen. "Biological pacemaking: in our lifetime?", Heart Rhythm, Apr. 2005, pp. 418-428, vol. 2, No. 4, Departments of Pharmacology and Pediatrics, Center for Molecular Therapeutics, College of Physicians and Surgeons of Columbia University, New York, NY.
Hideko Kasahara et al. "Progressive atrioventricular conduction defects and heart failure in mice expressing a mutant Csx/Nkx2.5 homeoprotein", The Journal of Clinical Investigation, Jul. 2001, pp. 189-201, vol. 108, No. 2.
Vania L.F. Linhares et al. "Transcriptional regulation of the murine Connexin40 promoter by cardiac factors Nkx2-5, GATA4 and Tbx5", Cardiovascular Research 64, 2004, pp. 402-411.
Bauer et al., "Inhibitory G. Protein Overexpression Provides Physiologically Relevant Heart Rate Control in Persistent Atrial Fibrillation" *Circulation*, Nov. 9, 2004; 110(19):3115-3120. Epub Oct. 25, 2004.
Bunch et al., "Impact of Transforming Growth Factor-β1 on Atrioventricular Node Conduction Modification by Injected Autologous Fibroblasts in the Canine Heart" *Circulation*, May 30, 2006; 113(21):2485-2494. Epub May 22, 2006.

* cited by examiner

*Primary Examiner* — Peter Paras, Jr.
*Assistant Examiner* — David A. Montanari
(74) *Attorney, Agent, or Firm* — Carol F. Barry (57) ABSTRACT

A biologic intervention method and apparatus generates a persistent modification to an AV node that is physiologically stable after the agent has matured but is alterable with subsequent application of an agent. Specifically, the generic agent is used to modulate a node in a cardiac conduction system including rate control using one and a combination of a family of $K^+$ channel or equivalent. Specifically, the channel is implemented to slow conduction by generating an outward current during optimization of action potential and repolarization phase thus decreasing the current that is available to excite downstream cells. A Kv 1.3 channel, for example, may be used as the biologic channel. The invention enables reversal of the modulation or adjustment for various heart rates (BPM) based on medical and patient-specific needs.

1 Claim, 13 Drawing Sheets

Table 1: Various Kvα subunits and their regulatory subunits

| Family | α Subunit | Regulatory subunit |
|---|---|---|
| Kv1 (Shaker) | Kv1.1 | Kv β1 (Kv β1.1), KCNE4 |
|  | Kv1.2 | Kv β1.1 |
|  | Kv1.3 | KCNE4 |
|  | Kv1.4 | Kv β2 (Kv β2.1), Kv β3 |
|  | Kv1.5 | Kv β1.1, Kv β1.3, Kv β2 (Kv β2.2), Kv β3 |
|  | Kv1.6 |  |
|  | Kv1.7 |  |
|  | Kv1.8 |  |
| Kv2 (Shab) | Kv2.1 | Kv β4, KchAP, γ-subunits (?) |
|  | Kv2.2 | Kv β4, KchAP, γ-subunits (?) |
| Kv3 (Shaw) | Kv3.1 |  |
|  | Kv3.2 |  |
|  | Kv3.3 |  |
|  | Kv3.4 | KCNE3 |
|  | Kv1.4 |  |
| Kv4 (Shal) | Kv4.1 | γ-subunits (?) |
|  | Kv4.2 | γ-subunits (?), KCNE2 |
|  | Kv4.3 | γ-subunits (?) |
| Kv5-9 | eag,elk,arg1,arg2, erg3, KvLQT1 | Mink, MiRP |

FIG. 11

RATE CONTROL DURING AF USING CELLULAR INTERVENTION TO MODULATE AV NODE

FIELD OF THE INVENTION

The invention generally relates to cardiac arrhythmia control to affect a normal sinus rhythm. Specifically, the invention relates to the control of atrial fibrillation using biological intervention.

BACKGROUND

The heart consists of several distinct regions, each with its unique electrophysiological characteristics and functions. Specifically, cardiac activity is managed by highly specialized cells that trigger polarization and depolarization of the heart muscle to provide natural intrinsic pacing. While the sino atrial (SA) node is the primary pacemaking unit of the heart, the atrio-ventricular (AV) node acts as a gatekeeper or valve between the atria and ventricles and controls ventricular response to supraventricular activation. The valve function of the AV node arises from cells that have longer postrepolarization refractoriness and very low excitability, which limit the maximum number of impulses that can traverse to the ventricles. AV node lacks sodium ($Na^+$) channels, and conduction in the AV node is primarily governed by L-type $Ca^{2+}$ channels.

Biologic treatment of the conduction system of the heart requires the introduction of biologic agents that are compatible and adaptable to the highly specialized cardiac cells. Further, cardiac cells are highly differentiated across the conduction zone. The channels in the SA node, for example, are different from the channels in the AV node. Similarly, the type of channels and composition thereof vary across the conduction system of the heart and provide varying contractility properties to the cardiac muscles. Accordingly, managing the channels is key to controlling cardiac arrhythmias. Realizing this fact, Donahue et al (Nature Medicine; 6(2) 1395-1398) have disclosed an approach of decreasing L-type $Ca^{2+}$ current, by over expressing an inhibitory component of G-protein that modulates β-adrenergic response with an eventual goal of slowing the conduction in the AV node.

Currently, arrhythmias such as, for example, tachy and brady are managed using implantable devices. While these devices have proven to be excellent means for therapy delivery to manage cardiac disease, they do not reconstruct or restore a damaged conduction cellular structure to its normal condition. Conduction in cardiac tissue, including the AV node, involves cell-to-cell charge transfer. Charge from an upstream cell that has already been excited by a wave front initiated from the SA node is transferred to the next unexcited cell downstream thereby raising its intracellular and transmembrane potential. The downstream cell is excited when its transmembrane potential is raised to the $Na^+$ channel or L-type $Ca^{2+}$ channel (in the case of the AV node) threshold. As this downstream cell is excited, it relays charge to the next unexcited cell even further downstream. This process continues and results in continuous conduction at a macroscopic level, although the conduction at a microscopic scale is arguably saltatory in nature (Spach M S et al. 1990. *Ann N Y Acad Sci;* 591:62-74).

The microscopic and cellular basis of conduction gives insights into how the conduction can be influenced. One approach to manipulate cardiac conduction is to impose greater load on each cell so that charge transfer to the next unexcited cell downstream is slowed, thereby delaying its rise to excitation threshold and decreasing macroscopic conduction velocity. A greater electrotonic load on the AV node cells can be imposed by implanting inexcitable cells in the AV node that can sink current but are incapable of sourcing out current because of their inability to fire an action potential. Fibroblasts either autologously derived from the patient (e.g. by taking a muscle biopsy) or commercially obtained, can be one such cell type. However, if implanted in their native form, fibroblasts may couple poorly or fail to couple altogether with the AV node cells. To facilitate coupling, fibroblasts can be transfected ex-vivo with Cx43 (or other Cx isoforms like Cx40 and Cx45) before they are implanted into the AV node. To further increase the potency of electrotonic load they possess, fibroblasts may be transfected with voltage gated potassium channels [e.g. Kv2.1, which encodes for $I_{K1}$ and Kv1.3, which encodes for another type of voltage dependent $K^+$ channel (Feld Y et al. 2002. Circulation. 105: 522-529)]. As the charge is transferred to fibroblasts and their transmembrane potential raised, these channels open-up and produce outward current and hence can act to amplify the loading effect offered by fibroblasts.

Atrial fibrillation (AF) is a disease of epidemic proportions with over 2 million people affected in US alone, and this number is expected to grow to 5 million by the year 2050. Its prevalence doubles with each decade of life from ~0.5% at age 50 to 9% at age 80. Present treatments are inadequate. Unlike ventricular arrhythmias, implantable devices are ineffective for treating atrial arrhythmias primarily because of their recurrent nature. Pharmacotherapy is the most common course of treatment for most patients. Two distinct treatment regimens are used—rhythm control and rate control. In rhythm control an effort is made to maintain the patient in sinus rhythm using cardioversion and antiarrhythmic drugs like amiodarone, sotalol and other class III drugs. In rate control the emphasis is on controlling the ventricular rate by modulating the AV node while letting the AF persist. Drugs like beta-blockers, diltiazem and verapimil are commonly used to achieve rate control. In the AFFIRM trial, a large (4060 patients) multicenter study comparing the two treatment strategies, no differences were found between the rhythm and rate control groups. In fact rate control group showed slightly lower mortality (the primary end point) although it did not reach statistical significance. Three other smaller trials (PIAF, RACE and STAF) reached the same conclusion i.e. no difference between rhythm and rate control groups. Moreover, in AFFIRM and PIAF trials that tracked hospital admissions, rate of hospitalization were statistically higher in rhythm control group than rate control.

Thus, rate control is an effective therapy for AF. Nevertheless, pharmacotherapy has several limitations. A subset (~5%) of patients do not tolerate commonly prescribed drugs, and pharmacotherapy eventually fails in 70-90% patients. Since the drugs are systemically taken, side effects are common. Further, cumulative cost of drugs when added over the entire lifetime of a patient (who generally are younger than those presenting with ventricular arrhythmias) can be quite staggering Hence there is a need for a system that can modulate the AV node and other cardiac conduction elements that may be damaged or malfunctioning. Further, there is a need to provide a systemic treatment of cardiac conductive tissue using biologic elements that cooperate with or influence the natural conduction channels in the heart.

The present invention addresses one or more of these needs. Furthermore, other desirable features and characteristics of the present invention will become apparent from the subsequent detailed description of the invention and the appended claims with the accompanying drawings and this background of the invention.

BRIEF SUMMARY OF THE INVENTION

In one exemplary embodiment, the electrotonic load on each AV nodal cell is increased, thereby decreasing cell-to-cell conduction and overall macroscopic conduction in the AV node.

In another exemplary embodiment a biologic technique is implemented for slowing the AV node conduction to control ventricular rate during atrial fibrillation.

In yet another exemplary embodiment, control of the transfection and expression levels of the channels in fibroblasts is implemented to extend the dynamic range of rate control of the cardiac conduction system.

An aspect of the present invention utilizes methods and process for implantation of fibroblasts (~$1 \times 10^6$ to $100 \times 10^6$ in number) transfected with connexin alone or with voltage gated potassium channels to modulate conduction in the AV node and provide rate control during AF. The implantation of these channels can be performed by one of a transvascular approach or via an AV nodal artery that specifically perfuses AV node or uses a direct endocardial injection into the AV node.

Another aspect of the invention provides a one-time biologic intervention to modulate AV node for rate control during AF. Specifically, a $K^+$ channel that would slow conduction by passing an outward current during action potential plateau and repolarizing phase is implemented to decrease the current available for excitation of downstream cells. The invention, for example, implements a Kv1.3 channel, a Shaker family channel that is quite abundant in several organ systems including the brain. The modeling study in a strand of Luo-Rudy model cell shows that the channel does produce slowing of conduction in a dose dependent manner.

BRIEF DESCRIPTION OF THE DRAWINGS

The present invention will hereinafter be described in conjunction with the following drawing figures, wherein the numerals denote like elements, and wherein:

FIGS. 2A and 2C show conduction in a normal tissue and FIGS. 2B and 2D show increase in conduction delays in presence of fibroblast. The length of arrows through the gap junctions represent amplitude of ionic current (I).

DETAILED DESCRIPTION OF THE INVENTION

The following detailed description of the invention is merely exemplary and is not intended to limit the invention or the application and uses of the invention. Further, there is no intention to be bound by any theory presented in the preceding background of the invention or the following detailed description of the drawings.

While the present invention is disclosed with reference to the AV node and specific channels it should be noted that other channels may be equivalently used and conduction systems such as the His Bundle and the Purkinje fibers may be modulated using the same or equivalent method and apparatus.

Figure 1:
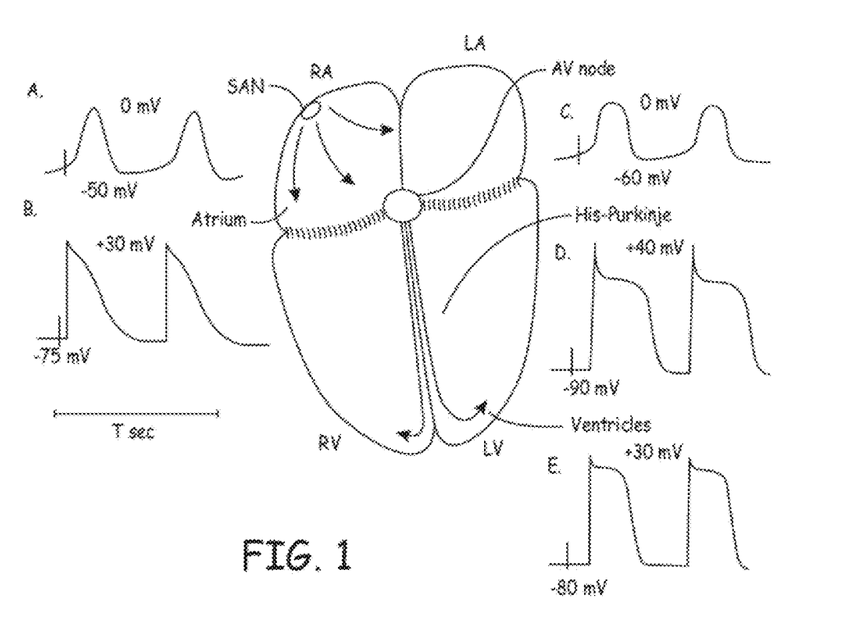
FIG. 1 is a schematic diagram depicting different electrophysiological characteristics of various regions of the heart.

Referring to FIG. 1, the four chambers of the heart and the various electrophysiological characteristics are shown. Specifically, the action potentials at the SA node, the AV node and His-Purkinje are shown. As can be seen the various regions of the heart have differing action potentials in both profiles and magnitude. Understanding these electrophysiological behaviors at the various conduction zones is key to designing a modulator agent that is custom-made to modify the functional aspects of the node.

Figure 2A:
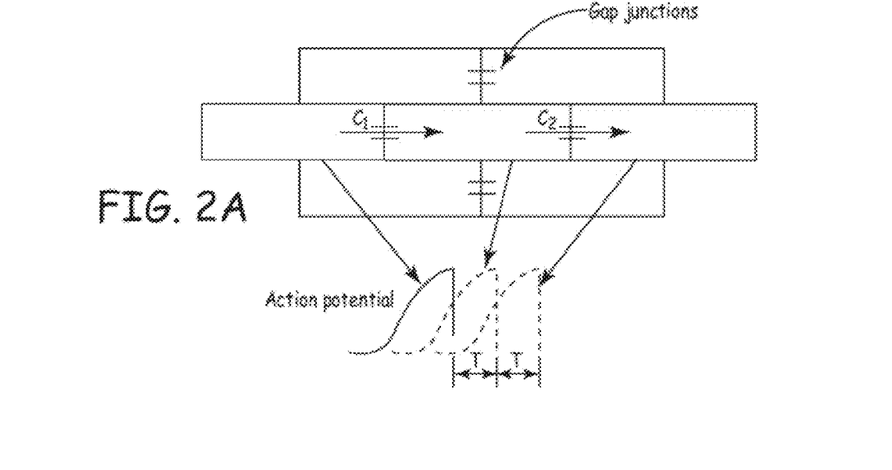
FIGS. 2A, 2B, 2C and 2D are schematic illustrations of the process of electrotonic load imposition by fibroblasts to slow cell-to-cell conduction thereby impacting macroscopic conduction. Specifically.

Referring to FIG. 2A, a linear strand of cardiac cells are represented. When cell C1, the leftmost cell in the strand, is excited it fires an action potential. This elevates the intracellular potential of cell C1 relative to cell C2. As a result current flows from cell C1 to cell C2 and the intracellular potential of cell C2 is elevated to the point where now cell C2 can fire an action potential. This sequential excitation of an upstream cell and current flow to the downstream cells for their excitation continues until all the cells in the strand are excited. The right panel shows the activation time for these cells and can be used to compute the conduction velocity (CV) once the length of each cell and overall strand is known ($CV=l/t_c$; where l is the length of strand and $t_c$ is the total activation time of the control strand).

Figure 2B:
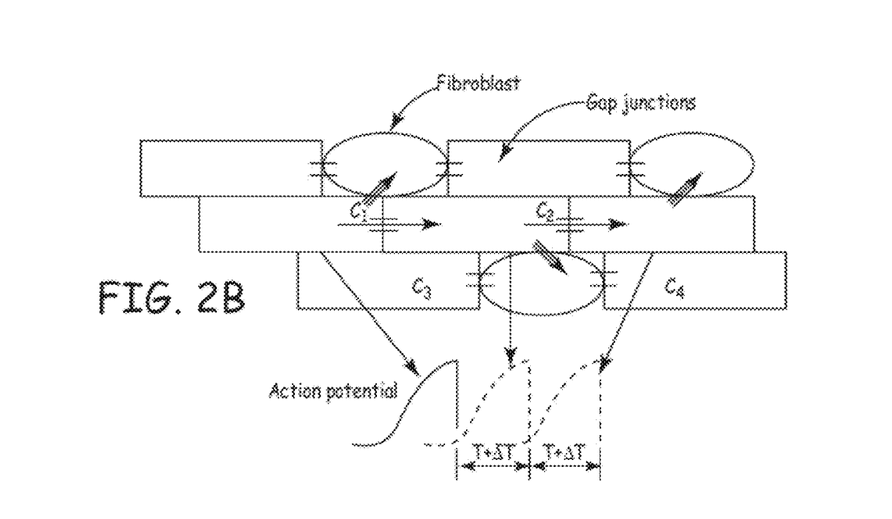
Figure 2C:
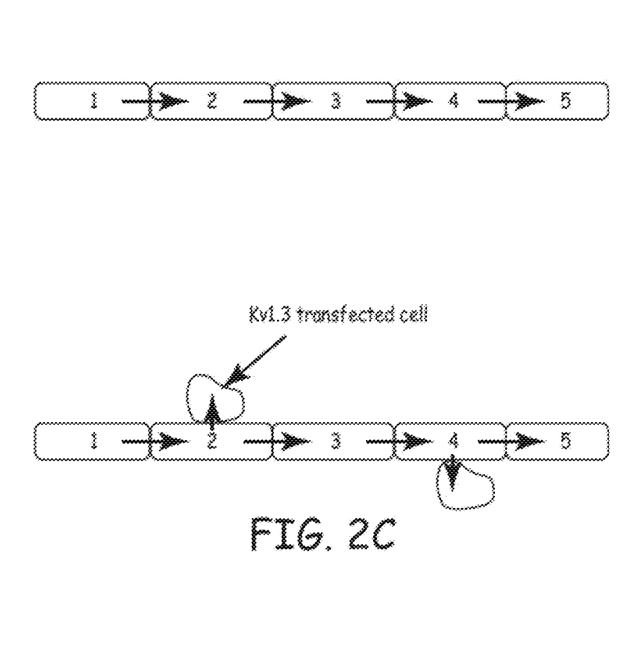
Figure 2D:
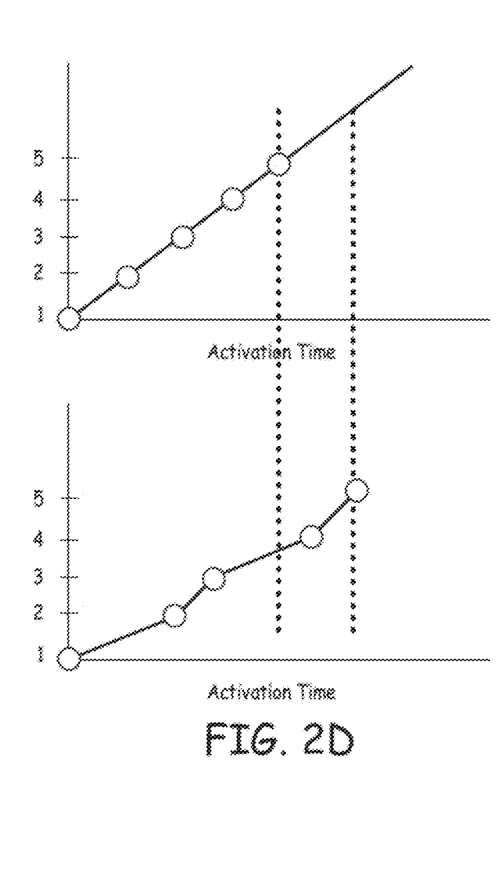

FIG. 2B shows the strand of cardiac cells with some of the cells in the strand having coupled to the exogenous cells carrying the gene Kv1.3. Similar to the disclosure hereinabove, when the cell C1 is excited, the voltage differential between the intracellular spaces of cell C1 and cell C2 provide current necessary for excitation of cell C2. However, because of the exogenous cell, which is coupled to the cardiac cell via gap junction channels, an electrotonic load is imposed on cell C2. Consequently, net current available for excitation of cell C2 is diminished and it takes longer for the cells to reach the excitation threshold (threshold for regenerative opening of $Na^+$ or $Ca^{2+}$ channels). A similar phenomenon is observed for excitation to be transferred from cell C3 to cell C4. FIG. 2C illustrates a similar slowing in a strand of cardiac cells. FIG. 2D shows the activation times and depicts that activation of transfected strand is significantly delayed compared to the control strand. The overall activation time of the transfected strand ($t_t$) is significantly delayed compared to the control strand (shown by dotted lines extending between the activation curves for control and transfected strands). Hence, the conduction velocity is slowed as well ($CV=l/t_t$). Although, FIG. 2 describes the concept using a cell approach, a similar effect would be observed with a gene approach (FIG. 2C)

where cell #2 and cell #4 express Kv1.3 channel; and other cells do not. If expression of Kv1.3 is uniform across the strand (as opposed to punctate where only some cells were transfected), the slowing of transfer of excitation would be accentuated.

Figure 3A:
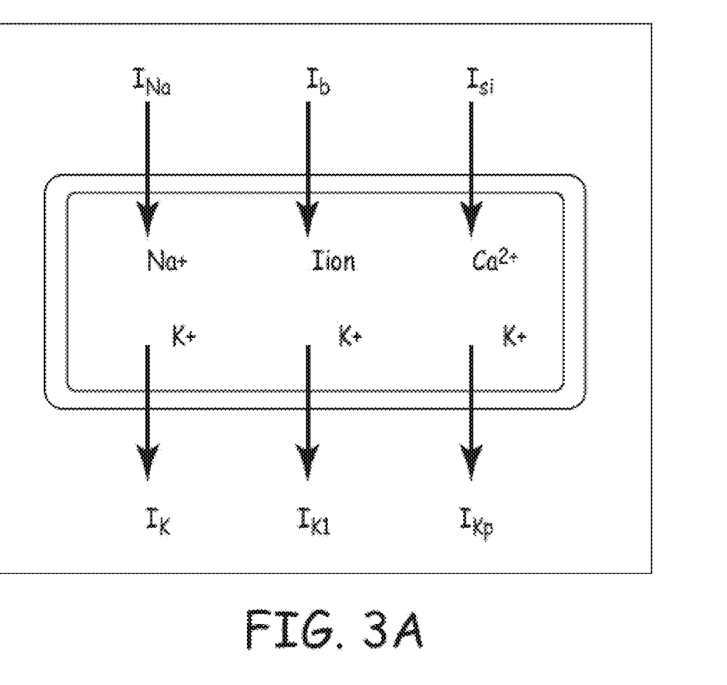
FIG. 3A illustrates Luo-Rudy model cell used to describe AV node modulation as implemented in the present invention.

FIG. 3A illustrates a Luo-Rudy ionic model. The model is implemented to simulate cardiac action potential in a single cell. In addition to sodium and potassium currents, the model represents processes that regulate intracellular calcium, sodium and potassium channels.

Figures 3B, 3C, 3D:
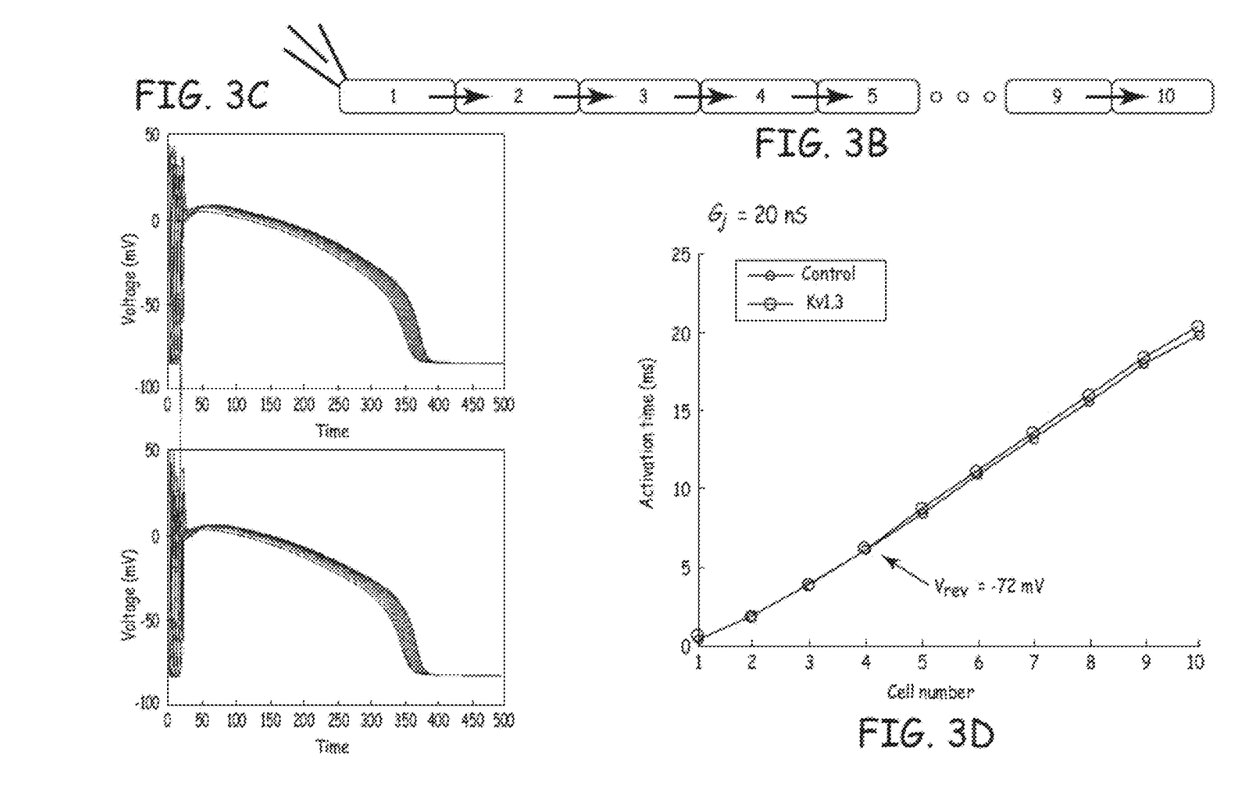
FIGS. 3B, 3C and 3D illustrate modeling results using the Luo-Rudy model as implemented in the present invention.

FIG. 3B illustrates the slowing of conduction in a model strand comprising of Luo-Rudy model cells. Electrophysiological basis of these cells comprise of six different currents. A strand of 10 cells is modeled with arrows indicating the direction of current flow. As described above, the leftmost cells are excited (using a current injection approach), and transfer of excitation from cell to cell is observed.

FIG. 3C illustrates the action potentials for the control strand and for a situation when the cells in the strand have uniformly been incorporated with Kv1.3 channels. The cells in the strand are assumed to be coupled via a gap junction conductance of 20 nS. FIG. 3D shows the activation times for a strand with and without (Control) Kv1.3. The activation time for the Kv1.3 strand is delayed by ~1 ms over 10 cells, a reduction of ~3%.

Figures 4A, 4B, 4C:
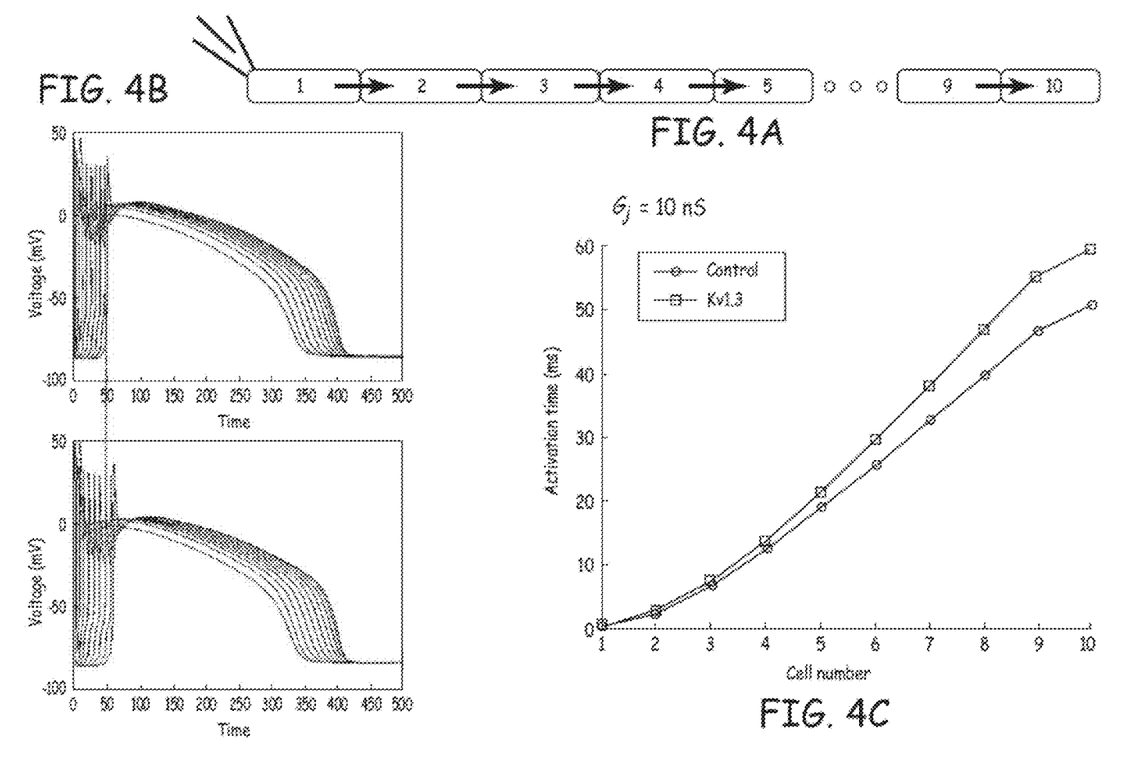
FIGS. 4A, 4B and 4C illustrate further modeling results using the Luo-Rudy model as implemented in the present invention.

FIG. 4 illustrates the effect of Kv1.3 transfection on the same strand as in FIG. 3B except that in this case the cell-to-cell coupling has been reduced to 10 nS (from 20 nS). Thus gap junction modulation in conjunction with Kv1.3 transfection can be used to produce slowing of conduction in the AV node or conduction in any other region of the heart. For the case depicted in FIG. 4 with reduced cell-to-cell coupling, the conduction delay over the expanse of 10 cells increased to ~10 ms. The percentage increase in conduction time over 10 cells was ~20%.

Figures 5A, 5B, 5C:
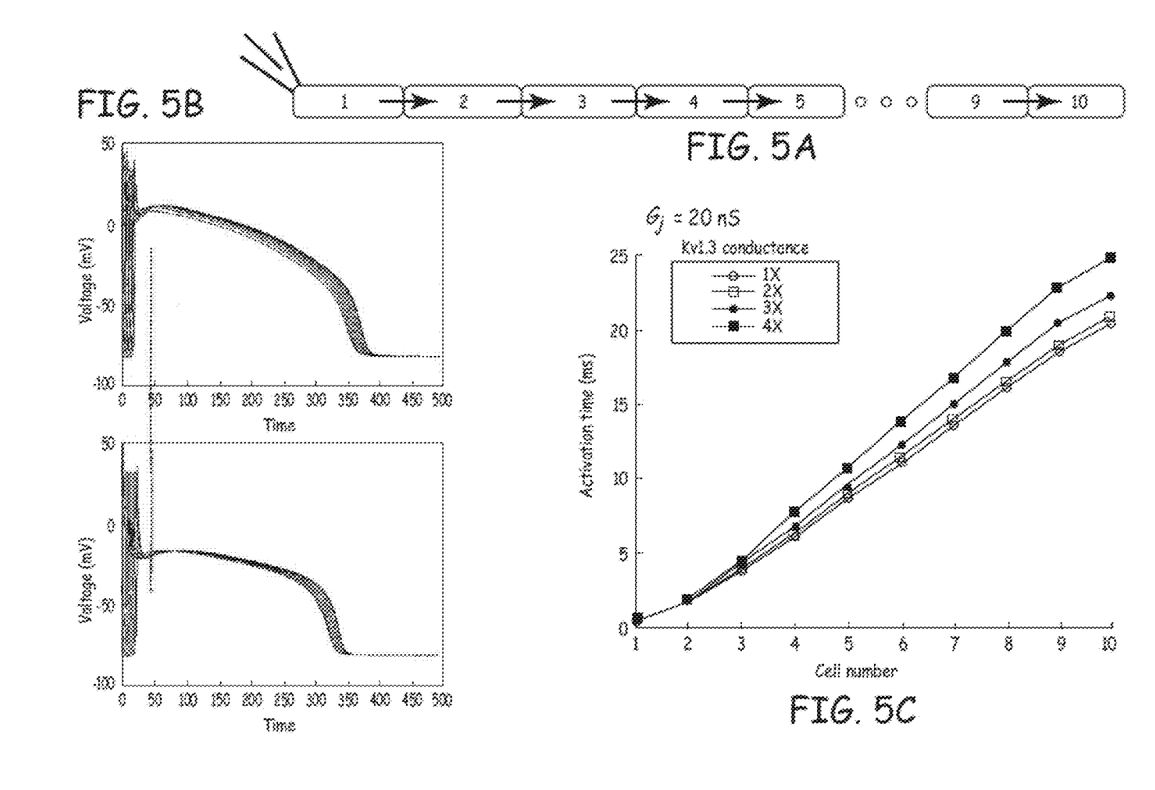
FIGS. 5A, 5B and 5C illustrate further modeling results using the Luo-Rudy model as implemented in the present invention.

FIG. 5 illustrates the dose-response effect of transfecting the linear strand. The curve with 1× conductance of Kv1.3 is same as that shown in FIG. 4. The other curves show the effect of increasing the amount of Kv1.3 in the strand by 2×, 3× and 4×. The conduction slowed in a dose dependent manner with larger doses of Kv1.3 producing larger slowing. For these simulation the Kv1.3 current was included in the Luo-Rudy model as follows:

$$I_{Kv1.3} = \overline{G}_{Kv1.3} K_{Kv1.3} (V - E_{Kv1.3})$$

Where: $\overline{G}_{Kv1.3} = 0.02$
$K_{Kv1.3} = 1/(1+\exp((3-(0.5*V_m))/5.98))$
$E_{Kv1.3} = R*T/F*\log(K_o/K_i)$
$K_o$: extracellular $K^+$ concentration and
$K_i$: intracellular $K^+$ concentration Gap junction conductance can be modulated by modulating the expression of connexin (Cx) molecules that underlie formation of these junctions. For the AV node conduction slowing application, Cx40 is the main target since it is the major Cx isoform found in the cardiac conduction system. However, other connexin isoforms can be targeted for other applications. For example, Cx43 can be downregulated in the slow conducting border zone of an infarct region that may be responsible for initiating and sustaining ventricular tachycardia. Connexin downregulation can be achieved by siRNA delivered via a viral vector or any other means. Alternatively appropriate short hairpin RNA can be delivered to interfere with the translation step of a specific connexin (e.g. Cx40 or Cx43). Other approaches may involve transfecting the region of interest with a dominant negative form of a transcription factors [e.g. Nkx2-5 and or GATA4 (Linhares et al. Cardiovasc Res. 64 (2004) 402-411; Kasahara et al. J. Clinical Invst. 108:2 (2001) 189-209] that regulate the expression of connexin molecules.

Figure 6:
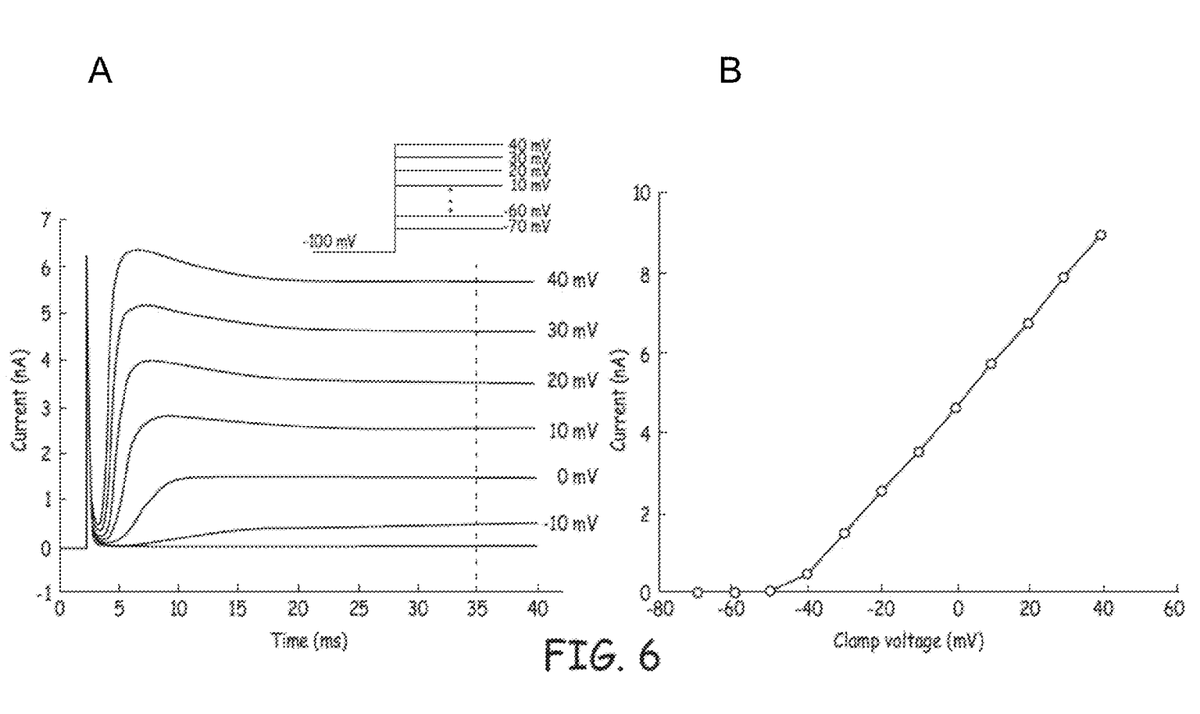
FIGS. 6 and 7 illustrate Kv1.3 characterization in accordance with the present invention.

FIGS. 6A and 6B illustrate the characterization of the Kv1.3 channels transfected in HEK cells using patch clamp technique. Specifically, FIG. 6A shows the raw current traces elicited by the voltage protocol shown in the inset chart starting at −100 mV and achieving a steep rise to 40 mV. FIG. 6B relates to the processed data, and indicates that the current during the step phase of the voltage protocol increases monotonically with the transmembrane voltage.

Figure 7:
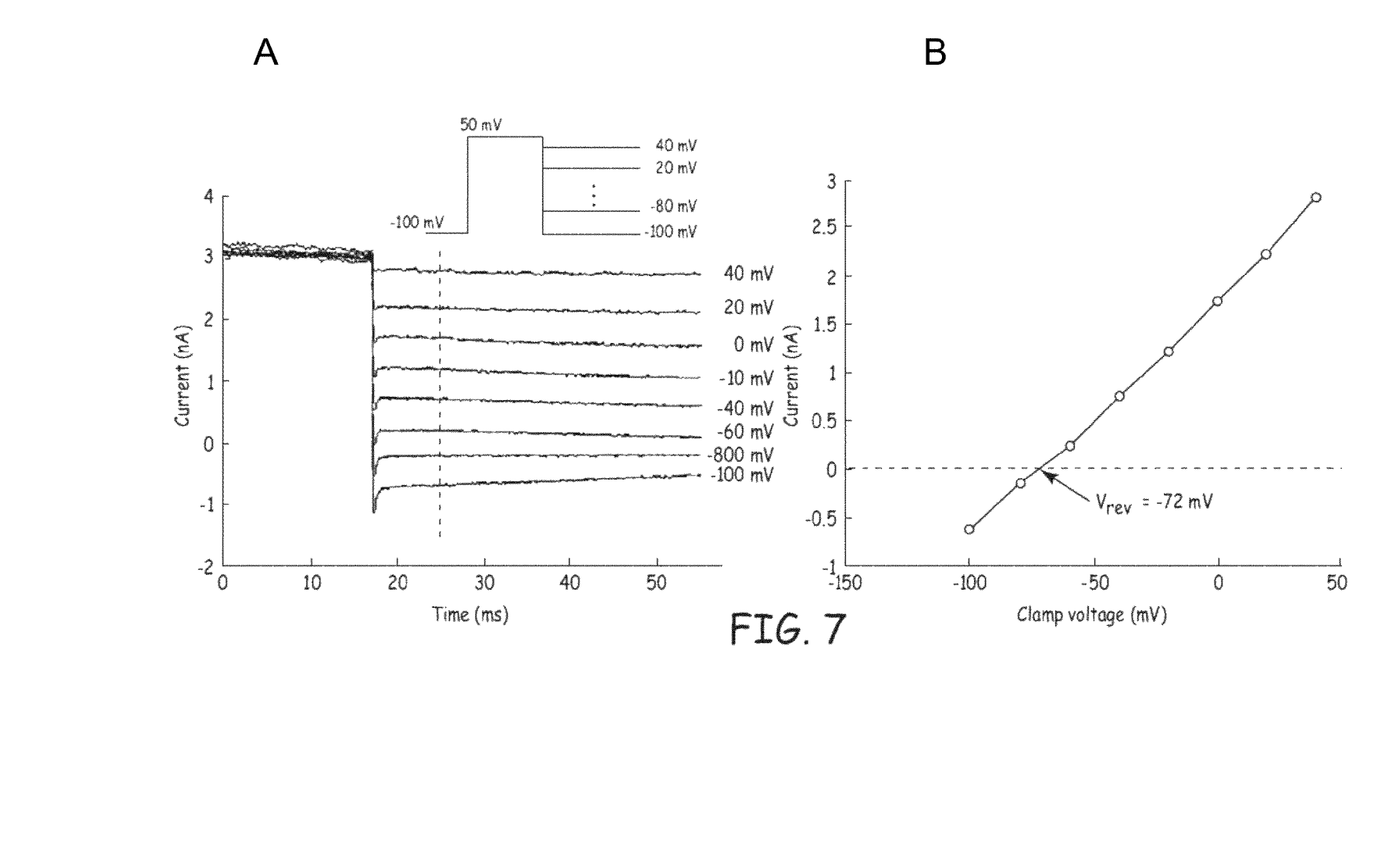

Referring now to FIGS. 7A and 7B the voltage protocol for measuring the instantaneous I-V relationship using patch clamp experiments is shown. Particularly, FIG. 7A provides the tail current after the pulse was measured (dotted line in left panel) and was plotted against the pulse voltage. The linear I-V relation, depicted in FIG. 7B, passes through the x-axis (0 current) at ~−72 mV, which is the reversal potential ($V_{rev}$) of Kv1.3 channels.

Figure 8A:
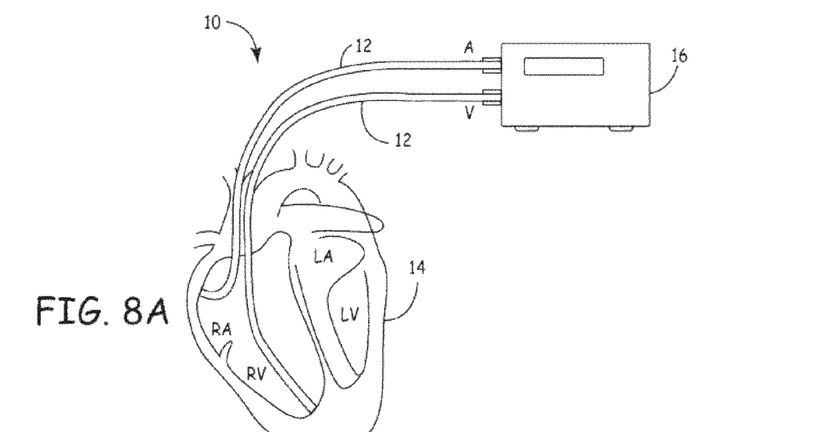
FIGS. 8A-8E illustrate apparatus and process for determining the gene or biologic dose tailored to a patient's condition.
Figure 8B:
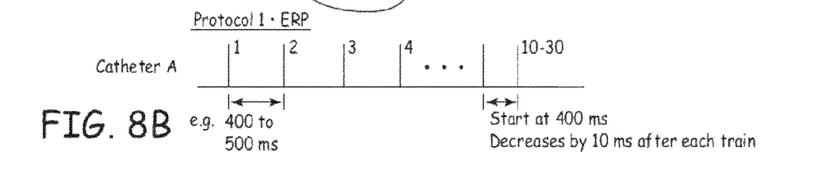
Figure 8C:
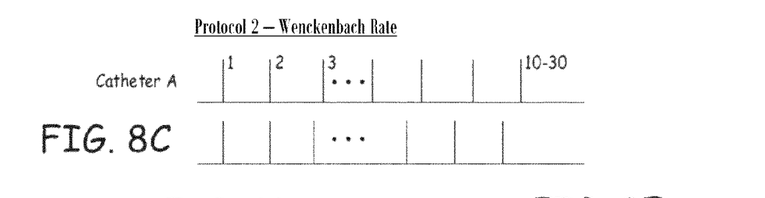
Figure 8D:
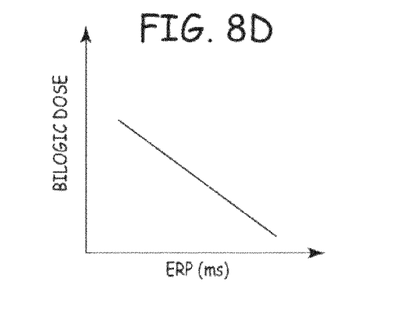
Figure 8E:
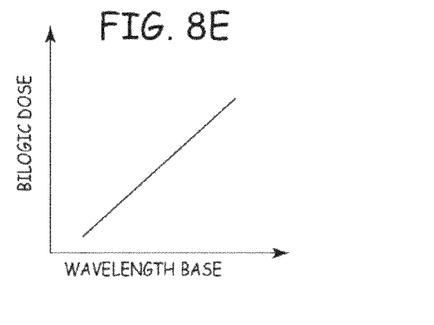

Referring to FIG. 8A, a system 10 is implemented to assess and determine the gene dose. The dose of the gene should be carefully titrated depending on the patient's need. In one embodiment of this invention the dose of the gene is dependent on the intrinsic conduction of the patient's AV node. The method of delivery of Kv1.3 to the AV node is critical for the success of the intervention. Accordingly, catheter/lead 12 is placed in the right atria and the right ventricle of heart 14, and catheters/leads 12 are then connected to device 16 that automatically performs a test to assess the intrinsic AV node conduction and recommend a gene dose based on predetermined formula in accordance with the graph of FIGS. 8B-8E. To assess the AV node conduction, for example, device 16 performs the EP study to determine the refractoriness based on effective refractory interval (ERP) and the Wenckebach rate. To measure ERP the atrium is paced at rapid rate for 10-30 pulses and the pulses of increasing prematurity are delivered to evaluate the coupling interval at which the conduction to the ventricle is blocked consistent with the chart shown in FIG. 8B. To measure Wenckebach rate the atrium is paced continuously at a rapid rate and this rate is gradually increased until the AV node fails to conduct in 1:1 fashion to the ventricle as shown in FIG. 8C. The dose of the biologic can be titrated either with ERP (FIG. 8D) or lowest pacing rate that produces Wenckebach phenomenon (FIG. 8E).

Figure 9A:
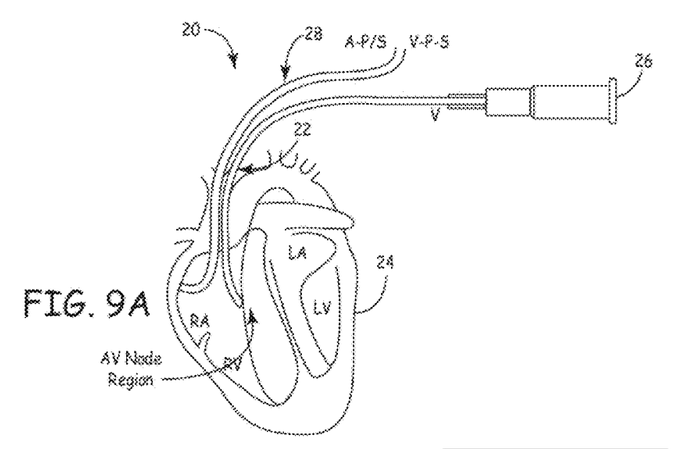
FIGS. 9A and 9B illustrate apparatus and process of injecting a bolus of biologic agent into the AV node.

Referring to FIG. 9A, a delivery system 20 for introducing exogenous genes to the AV node via catheter 22 is shown. Leads are positioned in the right atrium (RA) and right ventricle (RV) in heart 24. Catheter 22 capable of delivering the gene vector (or any other biologic) and measuring the electrical activity is placed in the AV node (triangle of Koch) region using an intravenous catheter placement procedure that is well known to persons skilled in the art. The catheter 22 may also be used for delivering acetylocholine or any other drug, if necessary. Syringe 26 is in fluid communication with catheter 22 to deliver the drug.

Figure 9B:
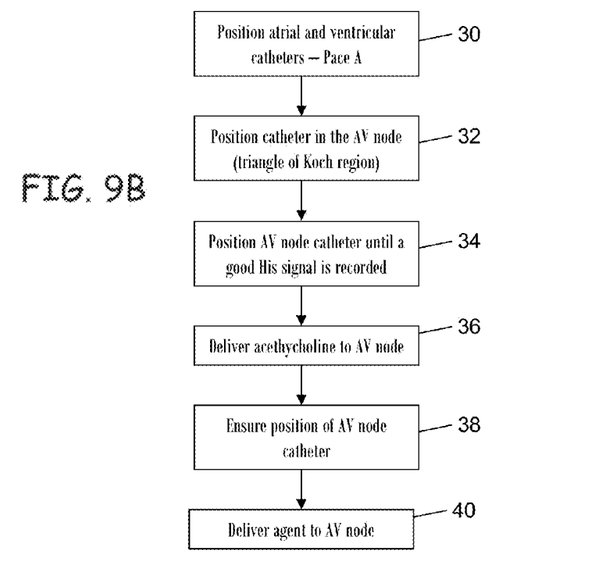

FIG. 9B illustrates a flowchart for a method of introducing a biologic agent into a cardiac conduction node. Specifically, under step 30 catheter 22 is placed in the right atria and right ventricle. Subsequently, under step 32 the placement of catheter 22 in the vicinity of the AV node region is ensured by recording/confirming, under step 34, a good His signal on the local ECG. The placement should be such that the amplitude of atrial and ventricular signals are approximately equal, if possible. Under step 36, a predefined bolus of acetylcholine, a negative chronotropic agent, is delivered to the AV node. Prior to the bolus delivery heart 24 is paced at a predefined rate to remove sinus rate as variable. The duration and extent of reduction in ventricular rate (along with the intrinsic conduction of the AV node) are used to assess the proximity of the catheter to the true AV node. This is used to ensure that gene vector is being delivered in the right region, and also to perform further titration of the biologic dose, if necessary. Once the slowing of conduction from the atria to the ventricle is ensured, under step 38, the position of catheter 22 is set. Thereafter, the biologic is delivered to the AV node under step 40. It should be noted that the dose for slowing the heart rate is titrated in such a way that normal physically activity, for example, exercise is allowed. Accordingly, the titration may be set in the range of 120 BPM or less. Since the modulation is reversible, a higher or lower heart rate could be set by changing the dose based on patient needs and medical considerations. The atrial (RA) and ventricular (RV) leads 28 are connected to a small device (not shown) capable of backup pacing as is well known to persons skilled in the art. The pacing option is implemented in case an overdose of biologic is delivered resulting in a 2° or 3° block of the AV node. Further, the pacing option may be needed during a period of monitoring of the maturation of the biologic which lasts until expression of the exogenous channel is established.

Figure 10:
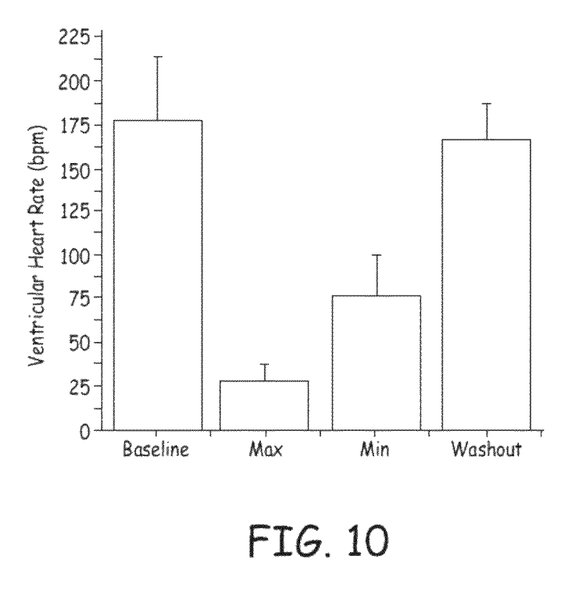
FIG. 10 illustrates the effect of acetylocholine on the ventricular rate.

FIG. 10 illustrates the results of an experiment in which acetylcholine was delivered locally to the AV node using a system and process similar to that described in FIGS. 9A and 9B. An acute episode of AF was induced and slowing of ventricular rate was observed under control conditions and with local injections of acetylocholine to the AV node. As illustrated, ventricular rate was reduced both at the maximum and minimum dose of acetylocholine that had a functional effect.

Another aspect of the invention is the biologic regulation of the effect of gene interpenetration in case it is found that the rate modulating effect of the gene is greater than desired. Most ion channels and transporters are modulated by their beta subunits. The gene for these subunits can be delivered to enhance or diminish the effect of main channel (typically the alpha subunit of the channel). In case of Kv1.3 the subunit KCNE4 diminishes the conductance of the main alpha subunit of the channel. Thus, if upon delivery of Kv1.3 it is found that the effect of the channel is more than desired, then a vector encoding for KCNE4 subunit can be delivered to diminish the effect of Kv1.3 and decrease its modulating effect on the AV node conduction.

Although in the above disclosure, Kv1.3 is the exemplary channel(s), other $K^+$ channels of the same family/subfamily can be used. Further, heteromeric channels formed by co assembly of Kv channel of different subfamily (e.g. Kv1.3 with Kv1.4) may be used to modulate the conductance and gating kinetics of resulting channels.

Figure 11:
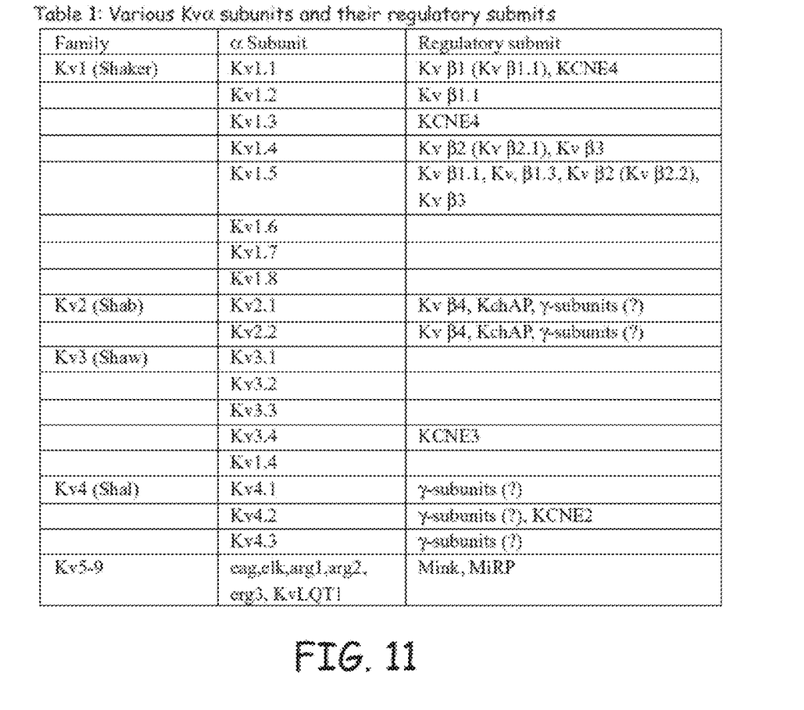
FIG. 11 illustrates families of Kva subunits as implemented in the present invention.

FIG. 11 (Table 1) provides a list of channels with the various modulatory subunits is presented for use in the present invention. The various subunits can be used in their wild type form or suitably mutated form. Further, regulation by β-subunits (regulatory subunits), the channel activity of main subunit can also be modulated by mutating the channel so that its basal phosphorylation state and/or its phosphorylation by enzymes such as protein kinase A (PKA) and protein kinase B (PKB) is altered or modified.

While exemplary embodiments have been presented in the foregoing detailed description of the invention, it should be appreciated that a vast number of variations exist. It should also be appreciated that these exemplary embodiments are only examples, and are not intended to limit the scope, applicability, or configurations of the invention in any way. Rather the foregoing detailed description will provide those skilled in the art with a convenient road map for implementing a preferred embodiment of the invention. It being understood that various changes may be made in the function and arrangement of elements described in an exemplary preferred embodiment without departing from the spirit and scope of the invention as set forth in the appended claims.

The invention claimed is:

1. A system comprising:
    a catheter sufficient to deliver a biological agent to the atrio-ventricular node of the heart of a subject;
    a device for pacing the heart rhythm of said subject; and
    a biological intervention agent that controls the ventricular rate during atrial fibrillation, wherein said biological intervention agent comprises a voltage gated potassium channel that is Kv2.1 or Kv1.3.

* * * * *